United States Patent [19]

Waldroup et al.

[11] Patent Number: 5,895,921

[45] Date of Patent: *Apr. 20, 1999

[54] METHOD AND SYSTEM FOR FECAL DETECTION

[75] Inventors: Amy Waldroup; John Kirby, both of Fayetteville, Ark.

[73] Assignee: The Board of Trustees of the University of Arkansas

[*] Notice: This patent is subject to a terminal disclaimer.

[21] Appl. No.: 08/829,781

[22] Filed: Mar. 31, 1997

Related U.S. Application Data

[62] Division of application No. 08/483,120, Jun. 7, 1995, Pat. No. 5,621,215.

[51] Int. Cl.$^6$ .................. G01N 21/64; G01N 33/12
[52] U.S. Cl. .................. 250/461.2; 250/459.1; 250/359.1; 250/910
[58] Field of Search .................. 250/461.1, 461.2, 250/458.1, 459.1, 359.1, 910; 209/577, 578

[56] References Cited

U.S. PATENT DOCUMENTS

| | | |
|---|---|---|
| 3,067,328 | 12/1962 | Harrison . |
| 4,622,469 | 11/1986 | Akiyama .................. 250/458.1 |
| 4,631,413 | 12/1986 | Jensen et al. .................. 250/910 |
| 4,778,999 | 10/1988 | Fisher .................. 250/461.1 |
| 4,782,234 | 11/1988 | Chudyk et al. . |
| 4,800,282 | 1/1989 | Nishimura .................. 250/461.1 |
| 4,866,283 | 9/1989 | Hill, Jr. .................. 250/461.2 |
| 5,305,893 | 4/1994 | Hereford .................. 209/577 |
| 5,419,438 | 5/1995 | Squyres et al. .................. 250/461.1 |
| 5,464,981 | 11/1995 | Squyres et al. .................. 250/910 |
| 5,474,910 | 12/1995 | Alfano . |
| 5,526,437 | 6/1996 | West .................. 209/577 |
| 5,621,215 | 4/1997 | Waldroup et al. .................. 250/359.1 |

*Primary Examiner*—Edward J. Glick
*Assistant Examiner*—Darren M. Jiron
*Attorney, Agent, or Firm*—J.M. (Mark) Gilbreth; Robert W. Strozier; Gilbreth & Strozier, P.C.

[57] ABSTRACT

A method of and apparatus for detecting the presence of fecal or ingesta matter contaminants on a poultry or meat item. The poultry or meat is conveyed in front of a UV light transmitter/receiver where UV light is directed onto the poultry or meat item and subsequently light is gathered from the poultry or meat. The gathered light is then compared to a threshold, above which indicates contaminants. If contaminants are present, the controller can generate a signal and/or send the contaminated items to a wash station.

5 Claims, 1 Drawing Sheet

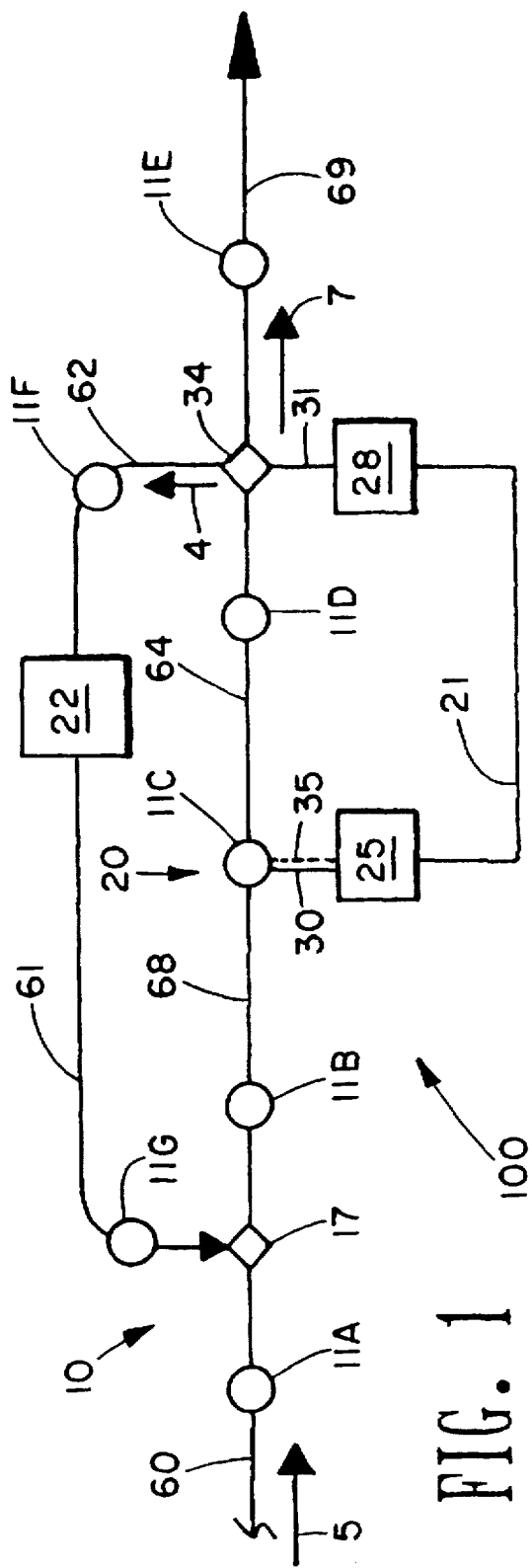
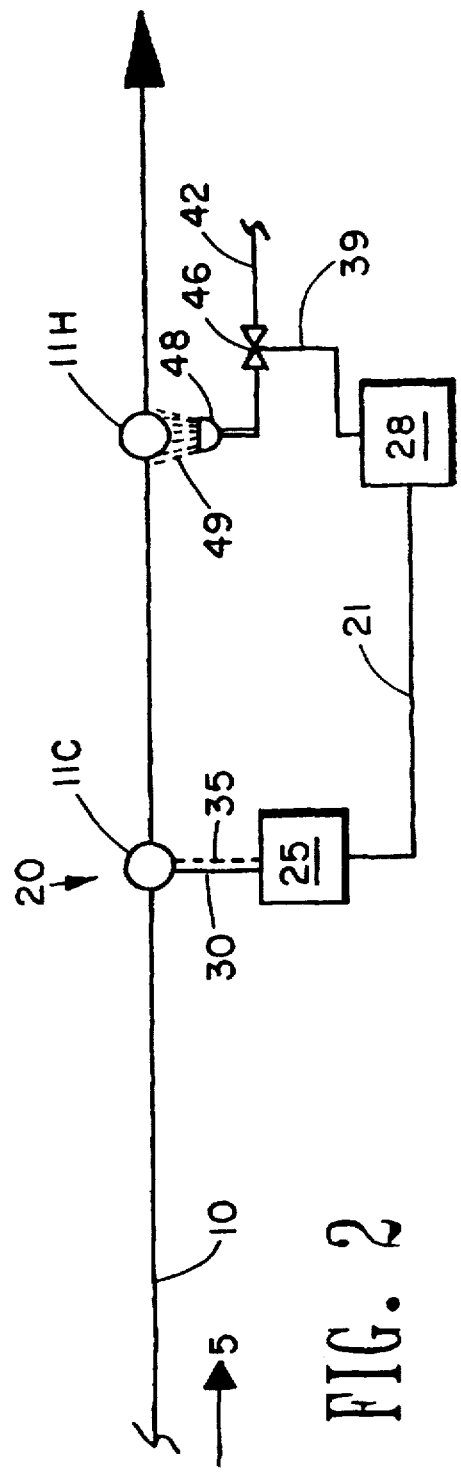

METHOD AND SYSTEM FOR FECAL DETECTION

This is a division of application Ser. No. 08/483,120 filed Jun. 7, 1995, now U.S. Pat. No. 5,621,215.

BACKGROUND OF THE INVENTION

1. Field of the Invention

The present invention relates to a method of and system for detection of fecal and ingesta material. In another aspect, the present invention relates to a method of and system for detection of fecal and ingesta material during the processing of foods. In even another aspect, the present invention relates to a method of and system for detection of fecal and ingesta material during the processing of poultry, beef, veal, pork, lamb and mutton. In still another aspect, the present invention relates to a method of and system for detection of fecal and ingesta material during the processing of poultry, beef, veal, pork, lamb and mutton, utilizing fluorescence.

2. Description of the Related Art

Processing of meats and poultry, such as chicken, turkey, beef, veal, pork, lamb, mutton, and even the more exotic emu and ostrich, tend to expose them to fecal and ingesta matter. This is especially true when meats and poultry are processed utilizing highly automatic and rapid systems which might cut into or tear apart the intestines and bowels of those animals. Additional expose to fecal matter occurs as a matter of course from having these animals confined immediately prior to slaughter in holding pens.

Inspection of meat and poultry has always been of great importance to insure the safety of the food system. However, in spite of the importance of having proper inspections, the advances in meat and poultry inspection technology have been limited at best.

Recent meat contamination events involving *e coli* bacteria have led the public and media to require more careful inspection of meat and poultry. Such publicity has also revealed to the public that inspection for bacterial contamination is many times conducted by a meat inspector using human sight to find microscopic bacteria and other contaminants. Such techniques reveal those meat and poultry carcasses in the advanced stages of contamination, but are not very efficient at finding less advanced stages of bacterial contamination.

With modern processing equipment and the economic demands of the market place, meat and poultry lines are typically run as quickly as possible, further complicating the task of human visual inspection.

There have been suggestions in the prior art for methods of inspecting foodstuffs.

Foods and feeds have natural components which fluoresce when exposed to energy at particular wavelengths. Coumarins, coumarosteroids, carotenoids, chlorophyllins, and other plant and animal pigments all have characteristic absorption and fluorescent properties. Fluorescence is commonly used to detect mouse and rat droppings in grain products, to detect the presence of *Aspergillus flavus* in various grain products, and to detect the spoilage organism, Pseudomonas in coolers and freezers.

U.S. Pat. No. 3,067,328, issued Dec. 4, 1962 to Harrison, discloses a method for the inspection of crustaceans to determine their freshness. The method involves exposing the shrimp to light in the violet and ultraviolet region of the spectrum of 250 to 375 millimicrons, and comparing the resultant fluorescence pattern against the bright white pattern for fresh shrimp.

U.S. Pat. No. 4,622,469, issued Nov. 11, 1986 to Akiyama, discloses a method of and apparatus for detecting rotten albumen. The apparatus includes a device for casting 300 to 410 nm UV light onto the albumen, an optical filter system for filtering out UV light at wavelengths less than 400 nm, and a discriminating means which compares the received signal to a predetermined threshold level of fluorescence from sound albumen, and after the comparison outputs a signal indicating the presence or absence of rotten albumen.

However, in spite of these advancements in the prior art, none of these prior art references disclose or suggest a method of or apparatus for inspecting meat and poultry for ingesta and fecal matter.

Thus, these is still a need for a method of and apparatus for inspecting meat and poultry.

There is another need in the art for method of and apparatus for inspecting meat and poultry that will not have an undue slowing affect on the processing speed.

There is even another need in the art for an economic method of and apparatus for inspecting meat and poultry.

There is still another need in the art for a method of and apparatus for inspecting meat and poultry, that has an improved detection method as compared to human visual inspection.

These and other needs in the art will become apparent to those of skill in the art upon review of this specification, including its drawings and claims.

SUMMARY OF THE INVENTION

It is an object of the present invention to provide for a method of and apparatus for inspecting meat and poultry.

It is another object of the present invention to provide for a method of and apparatus for inspecting meat and poultry that will not have an undue slowing affect on the processing speed.

It is even another object of the present invention to provide for an economic method of and apparatus for inspecting meat and poultry.

It is still another object of the present invention to provide for a method of and apparatus for inspecting meat and poultry, that has an improved detection method as compared to human visual inspection.

These and other objects of the present invention will become apparent to those of skill in the art upon review of this specification, including its drawings and claims.

According to one embodiment of the present invention there is provided a method for detecting the presence of fecal or ingesta matter contaminants on a poultry or meat item. The method includes shining an ultraviolet light onto the poultry or meat item. Next, the method includes gathering light fluorescing or otherwise emanating from the poultry or meat item. The method also includes producing a signal indicative of the presence of contaminants if the gathered ultraviolet light has fluorescence greater than a target threshold.

According to another embodiment of the present invention there is provided an apparatus for detecting the presence of fecal or ingesta matter contaminants on a poultry or meat item. The system generally includes a conveyer system for moving the poultry or meat item along a pathway. The system also includes an ultraviolet light transmitter positioned adjacent the path to transmit light onto the poultry or meat item as it passes by the transmitter. The system additionally includes a light receiver for gathering light reflected from the poultry or meat item. The system still additionally includes a processor for comparing the light gathered in step(c) against a threshold fluorescence. As separate optional embodiments, the system may also include signal generator for generating a signal indicative of the presence of contaminants if the light gathered in step(c) is greater than a threshold fluorescence, and for generating a signal indicative of the absence of contaminants if the fluorescing light gathered in step(c) is less than a threshold fluorescence. The system may also include a wash system that either washes or sprays the contaminated poultry or meat.

BRIEF DESCRIPTION OF THE DRAWINGS

FIG. 1 is a schematic representation of one embodiment of inspection system 100 of the present invention, showing conveyer line 10, UV light transmitter/receiver 25, computer controller 28, switching station 34, and rewash station 22.

FIG. 2 is a schematic representation of another embodiment of inspection system 100 the present invention, showing conveyer line 10, UV light transmitter/receiver 25, computer controller 28 and rewash sprayer 48.

DETAILED DESCRIPTION OF THE INVENTION

The method of the present invention generally includes exposing meat or poultry to ultraviolet light, determining if the resultant fluorescence is within certain wavelengths which indicate the presence of fecal or ingesta material, and generating a signal to rewash or otherwise reject the meat or poultry. "Meat" as used herein is to be taken to refer broadly to food products derived from livestock or game animals, including the following nonlimiting examples of beef, pork, veal, lamb, mutton, venison, boar, and the like. "Poultry" as used herein is to be taken to refer broadly to food products derived from birds, including the following nonlimiting examples of chicken, turkey, pheasant, duck, quail and even the more exotic emu and ostrich. The present invention is preferably utilized to process turkey and chicken, most preferably chicken.

While not wishing to be limited by theory, the inventors have determined that a component in poultry feces and in excreta from the crop of broilers (chicken), is fluorescent under ultraviolet or "black" light. This component is believed to be a carotenoid or retinoid. Additionally, after the feces or crop excreta have been washed or rinsed (with either tap water or chlorinated water—20 ppm) from the surface of the product, the fluorescent characteristics are still visible under black light. Thus, if a carcass is contaminated with fecal material or excrement from the crop during the slaughter process, this could be determined using the ultraviolet light. Intensity of the fluorescence after rinsing increases with time of exposure of the materials (feces or crop excrement) to the food surface but is easily visible even after a 15-second exposure period. The inventors also note that fecal material that is dried out (more than a few hours old) does not fluoresce as well as fresh feces.

The present invention will now be further described by reference to FIGS. 1 and 2. Referring first to FIG. 1, there is shown one embodiment of system 100 of the present invention, showing conveyer line 10, UV light transmitter/receiver 25, computer controller 28, merge station 17, switching station 34, and rewash station 22.

In FIGS. 1 and 2, items 11A–H will be referred to as chicken 11, although it is to be understood that item 11 could be any poultry or meat, including those described above.

Chicken 11A–H progresses along conveyer system 10 in the general direction of arrow 5 as shown.

Chicken 11A is shown as entering conveyer system 10 on conveyer section 60. Conveyer systems are well known in the art of processing poultry and meat. In the practice of the present invention, the specific type of conveyer system 10 is not critical. Thus, any suitable system may be utilized as conveyer system 10.

Chicken 11G is returning on conveyer section 61 from rewash station 22 where it was subjected to additional washing after fecal or ingesta material was detected. Chicken 11G will return to conveyer portion 60 via merging station 17.

Chicken 11B is shown approaching, and chicken 11C is shown in detection area 20 where UV light 35 is transmitted by UV light transmitter/receiver 25 onto the chicken to be inspected. Fluorescing light 30 is received by UV light transmitter/receiver 25.

In the practice of the present invention, the wavelength of UV light utilized must be suitable to cause fluorescence upon striking fecal or ingesta matter, which fluorescence must be sufficient for detection. Generally, the wavelength of light transmitted by transmitter/receiver 25 will be in the range of about 320 nm to about 420 nm. Preferably, the wavelength of light transmitted by transmitter/receiver 25 will be in the range of about 350 nm to about 375 nm, and more preferably in the range of about 360 to about 370 nm.

While the embodiment of the present invention is illustrated in FIG. 1 as having one instrument, UV light transmitter/receiver 25, for both the generation of UV light and for light gathering, it is to be understood that the invention is not so limited and that dedicated transmitters and receivers could be utilized. The received light 30 generates a signal 21 which is relayed to computer or controller 28.

Additionally, while the present system 100 is illustrated as having one transmitter and one receiver, it is envisioned that any suitable number of transmitter and receivers may be utilized. In fact, to cover a greater percentage of the surface are of the chicken, and thus increase the quality of the inspection, it is preferred that two or more transmitters and receivers be utilized.

The fluorescing light 30 may be received by any suitable receiver. Preferably the receiver 25 is a camera type device which will digitize received signal 30 for processing. Most preferably, a signal pixel width camera will be utilized.

Computer or controller 28 will compare the received wavelength against a threshold value to determine if fecal or ingesta matter is indicated.

Chicken 11D is shown as approaching switching station 34 which is controlled by computer 28. For chicken which were indicated as having fecal or ingesta material, i.e., chicken 11F, computer 28 provides a signal via connection 31 to switching station 34 to route the chicken to rewashing station 22 on alternative pathway conveyer 64. Of course, while the present invention is illustrated in terms of a rewashing for chicken indicating presence of fecal or ingesta matter, it is to be understood that another alternative is to discard or manually process the chicken.

For chicken which were indicated as not having fecal or ingesta material, i.e., chickens 11E, computer 28 provides a signal via connection 31 to switching station 34 to route the chicken to conveyer 69 to continue for further processing.

After rewashing at rewashing station 22, the chicken then travels via conveyer 61 to merging station 17 to rejoin conveyer section 68.

Referring now to FIG. 2 there is shown a schematic representation of another embodiment of system 100 of the present invention, having conveyer line 10, fluorescence transmitter/receiver 25, computer controller 28 and rewash sprayer 48.

Chicken 11C is shown in detection area 20 where UV light 35 is transmitted by UV light transmitter/receiver 25 onto the chicken to be inspected. Fluorescing light 30 is received by UV light transmitter/receiver 25.

Again, computer 28 will compare the received wavelength against a threshold value to determine if fecal or ingesta matter is indicated. For chickens which were indicated as having fecal or ingesta material, i.e., chicken 11H, computer 28 provides a signal via connection 39 to open valve 46 of wash line 42, to provide cleaning spray 49 through nozzle 48. Any suitable number of wash sprays can be arranged around chicken 11H.

While the present invention has been illustrated as having chicken on a conveyor belt traverse in front of a stationary UV light transmitter 25, it is to be understood that the chicken could be stationary and UV light transmitter in motion, or both could be in motion.

While the present invention has been illustrated as having a UV light transmitter and receiver, it is to be understood that the present invention finds utility for enhancing human inspection of meat and poultry. For example, instead of a receiver, an inspector could monitor meat and poultry as it passed through inspection area 20. Additionally, the present invention could be incorporated into a hand-held or portable unit which could be utilized to inspect meat and poultry. Additionally, stationary units could be provided at points of sale for the peace of mind of the consumer to inspect meat or poultry immediately prior to purchase.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. A method for detecting the presence of fecal or ingesta matter contaminants on a poultry or meat item, the method comprising:

(a) directing an ultraviolet light having a wavelength in the range of about 350 nm to about 385 nm at the poultry or meat item;

(b) gathering light fluorescing from the poultry or meat item;

(c) producing a signal indicative of the presence of contaminants if the gathered light has fluorescence greater than a target threshold, the signal designating the poultry or meat item as a contaminated poultry or meat item;

(d) diverting the contaminated poultry or meat item for further processing.

2. The method of claim 1 wherein the ultraviolet light of step (a) has a wavelength in the range of about 350 nm to about 375 nm.

3. The method of claim 1 wherein the contaminated meat or poultry item of step (d) is further processed through steps (a), (b) and (d) until the light gathered in step (b) is below the target threshold.

4. An apparatus for detecting the presence of fecal or ingesta matter contaminants on a poultry or meat item, the system comprising:

(a) a conveyer system for moving the poultry or meat item along a pathway;

(b) an ultraviolet light transmitter positioned adjacent the path to transmit light having a wavelength in the range of about 350 nm to about 385 nm onto the poultry or meat item;

(c) a light receiver for gathering light fluorescing from the poultry or meat item;

(d) a processor for comparing the fluorescing light gathered in step(c) against a threshold fluorescence;

(e) signal generator for generating a signal indicative of the presence of contaminants if the fluorescing light gathered in step(c) has a fluorescence greater than a threshold fluorescence, and for generating a signal indicative of the absence of contaminants if the fluorescing light gathered in step(c) has a fluorescence less than a threshold fluorescence;

(f) a diverter for diverting the poultry or meat if the signal generator generates a signal indicative of the presence of contaminants.

5. The apparatus of claim 4 wherein the light transmitter transmits light having a wavelength in the range of about 350 nm to about 375 nm.

* * * * *